(12) United States Patent
Hiramatsu et al.

(10) Patent No.: US 8,940,231 B2
(45) Date of Patent: Jan. 27, 2015

(54) MEASURING EQUIPMENT AND MEASURING METHOD USING CARTRIDGE CONTAINER, AND PROGRAM RECORDING MEDIUM

(75) Inventors: Hisao Hiramatsu, Kyoto (JP); Hiroshi Fukuya, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1041 days.

(21) Appl. No.: 11/705,359

(22) Filed: Feb. 12, 2007

(65) Prior Publication Data

US 2007/0148052 A1 Jun. 28, 2007

Related U.S. Application Data

(62) Division of application No. 10/049,798, filed as application No. PCT/JP01/04514 on May 29, 2001, now abandoned.

(30) Foreign Application Priority Data

Jun. 12, 2000 (JP) .................................. 2000-175647

(51) Int. Cl.
*G01N 35/00* (2006.01)
*B01L 3/00* (2006.01)
(Continued)

(52) U.S. Cl.
CPC .............. *B01L 3/545* (2013.01); *G01N 35/026* (2013.01); *G01N 2035/00752* (2013.01); *G01N 2035/0436* (2013.01)
USPC ........................................... 422/62; 436/180

(58) Field of Classification Search
CPC ..................... B01L 3/545; G01N 2035/00752; G01N 2035/0436; G01N 35/026
USPC ......................................................... 422/62
See application file for complete search history.

(56) References Cited

U.S. PATENT DOCUMENTS 5,116,576 A * 5/1992 Stanley ............................ 422/55
5,174,961 A * 12/1992 Smith ............................... 422/73
(Continued)

FOREIGN PATENT DOCUMENTS

EP 0 895 088 2/1999
JP 58-36359 3/1983
(Continued)

OTHER PUBLICATIONS

The Free-Online Dictionary of Computing, Oct. 21, 1998.
(Continued)

*Primary Examiner* — Paul Hyun
(74) *Attorney, Agent, or Firm* — Morgan, Lewis & Bockius LLP

(57) ABSTRACT

In the measuring equipment, a nozzle driving unit 10 equipped with a bar code reader decides whether the cartridge container being set is a special-purpose container, in which a predetermined reagent is injected separately in advance and to which a bar code is attached, or a general-purpose container that is prepared by separately injecting reagents by hand into an empty cartridge container, and when the cartridge container is a special-purpose container, a CPU 1 reads out measurement conditions from a measurement condition storage part for special-purpose reagents 3*a* based on the information included in the bar code, and when the cartridge container is a general-purpose container, the CPU1 reads out measurement conditions for items of a measurement object selected and input by a measurer from a measurement condition storage part for general-purpose reagents 3*b* to conduct a measurement.

8 Claims, 10 Drawing Sheets

(51) Int. Cl.
*G01N 35/02* (2006.01)
*G01N 35/04* (2006.01)

(56) References Cited

U.S. PATENT DOCUMENTS

| | | | |
|---|---|---|---|
| 5,358,691 A * | 10/1994 | Clark et al. | 422/64 |
| 5,374,395 A | 12/1994 | Robinson et al. | |
| 5,597,702 A * | 1/1997 | Wong et al. | 435/18 |
| 5,800,784 A * | 9/1998 | Horn | 422/535 |
| 5,948,359 A | 9/1999 | Kalra et al. | |
| 2001/0012612 A1 | 8/2001 | Petersen et al. | |
| 2001/0051377 A1 | 12/2001 | Hammer et al. | |
| 2002/0064884 A1 | 5/2002 | Devlin et al. | |

FOREIGN PATENT DOCUMENTS

| | | |
|---|---|---|
| JP | 1-312467 | 12/1989 |
| JP | 3-181853 | 8/1991 |
| JP | 8-122336 | 5/1996 |
| JP | 8-211071 | 8/1996 |
| JP | 9-127129 | 5/1997 |
| JP | 1-1316226 | 11/1999 |

OTHER PUBLICATIONS

The American Heritage Dictionary of the English Language, Fourth Addition, 2000.

* cited by examiner

MEASURING EQUIPMENT AND MEASURING METHOD USING CARTRIDGE CONTAINER, AND PROGRAM RECORDING MEDIUM

CROSS REFERENCE TO RELATED APPLICATIONS

This application is a Division of application Ser. No. 10/049,798, filed Feb. 12, 2002, which is a U.S. National Stage application of PCT/JP01/04514, filed May 29, 2001, which applications are incorporated herein by reference.

FIELD OF THE INVENTION

The present invention relates to measuring equipment and a measuring method using a cartridge container including a plurality of vessels into which separate liquid reagents are injected to measure a specific component contained in a specimen from a sample that is obtained by mixing a body fluid (specimen) such as blood or urine with reagents inside this cartridge container following predetermined processes.

BACKGROUND OF THE INVENTION

Conventionally, particularly in the field of clinical examinations, it is known to prepare a sample by mixing a specimen such as human blood or urine with a necessary reagent and to carry out an automatic measurement of a specific component from the specimen quantitatively by measuring the absorbance etc. of this sample.

Among such conventional measuring equipment, there are a special-purpose apparatus whose measurement object is limited to a specific substance and a general-purpose apparatus that is capable of measuring a wide range of substances. In the case of the special-purpose apparatus, a special-purpose cartridge container injected separately in advance with liquid reagents needed for measurement of items of a measurement object is already prepared. In this configuration, an operator only needs to fill a specimen into the special-purpose cartridge container and set this container in the equipment, and all the operations from mixing the reagents with the specimen to the measurement are carried out automatically inside one special-purpose cartridge container.

In the case of the general-purpose apparatus, on the other hand, it is necessary to use various kinds of reagents compared to the special-purpose apparatus. Therefore, it is difficult to automate all the operations, and the measurement operation procedures corresponding to the measurement object need to be determined by the operator. Furthermore, due to the fact that the larger. In addition, every time the measurement object is changed, it is necessary to replace reagents or to clean the apparatus, so that the loss of reagent is great, and also the consumables such as wash water are consumed in a large amount. Furthermore, every time the measurement object is changed, it is highly possible that corrections need to be made before measurements.

In other words, the special-purpose apparatus is of specific limited application, so that the following advantages are available: (1) it is generally smaller than the general-purpose apparatus; (2) it is possible to automate the operations almost completely; (3) it is not necessary to make corrections frequently before measurements; and (4) reagents are not changed frequently so that the amount of consumption for wash water etc. is less.

However, as a matter of course, the special-purpose apparatus can only carry out the measurement of a specific measurement object. Therefore, when a substance that cannot be measured by the special-purpose apparatus needs to be measured, there is no other way but to use the general-purpose apparatus in spite of the disadvantages described above.

DISCLOSURE OF THE INVENTION

It is an object of the present invention to solve the above-mentioned problems by providing measuring equipment constructed to use a predetermined cartridge container, which is excellent for general purpose use while maintaining the advantages of the special-purpose apparatus in that it is generally smaller than the general-purpose apparatus and capable of automating the operations almost completely.

To achieve the above-mentioned object, the measuring equipment of the present invention is measuring equipment for conducting a measurement using a cartridge container in which a specimen and a reagent are injected separately into a plurality of vessels, and the cartridge container is either a special-purpose cartridge container, which is injected separately in advance with predetermined reagents corresponding to items of a measurement object and sealed with a sealing material on which an information carrier including information relevant to the cartridge container is attached, or a general-purpose cartridge container that does not have the information carrier and is injected separately with reagents by a measurer. The equipment includes: carrier identification means for deciding whether an information carrier is attached to a cartridge container of a measurement object, measurement condition storage means for storing measurement conditions for each item of the measurement object, and operation control means that decides from an output of the carrier identification means whether the cartridge container of the measurement object is a special-purpose cartridge container or a general-purpose cartridge container, and when the cartridge container of the measurement object is a special-purpose cartridge container, a measurement is conducted according to measurement conditions read out from the measurement condition storage means based on the information included in the information carrier, whereas when the cartridge container of a measurement object is a general-purpose cartridge container, a measurement is conducted by outputting an instruction to select items of the measurement object to output means and reading out the measurement conditions from the measurement condition storage means for the items of the measurement object selected and input from input means.

According to this configuration, in the measuring equipment capable of measuring specific items of a measurement object using a special-purpose cartridge container that is injected separately in advance with predetermined reagents, also items other than the specific items of a measurement object can be measured using a general-purpose cartridge container, in which commercially available reagents etc. are injected separately as needed into an empty cartridge container by a measurer, so that measuring equipment that is excellent for general purpose use can be provided. Here, the "measurer" includes not only a person who actually conducts measurements while operating the present measuring equipment but also a person who conducts preparation works for measurements such as injecting a reagent or a specimen into a cartridge container.

In the aforementioned measuring equipment, it is preferable that the information carrier is an optically readable carrier, and optical read means is disposed in means for transferring liquid between the vessels of the cartridge container.

According to this configuration, it is possible to decide easily whether an information carrier is attached to the cartridge container. In addition, as the optically readable information carrier, for example, a bar code, a graphic character code, and other marks or the like can be used.

It is preferable that the aforementioned measuring equipment further includes information read means to read information from a magnetic recording medium, wherein the operation control means directs the information read means to read measurement conditions recorded in the recording medium and to store them in the measurement condition storage means.

According to this configuration, for example, a magnetic recording medium in which measurement conditions for items of a measurement object requested from a user is offered from a manufacturer of measuring equipment etc. to the user of the equipment, so that the measuring equipment corresponding to the needs of the user can be constructed easily. In addition, as the magnetic recording medium mentioned above, for example, a magnetic card or the like can be used.

In the aforementioned measuring equipment, it is preferable that the measurement condition storage means has a first area where measurement conditions for using the special-purpose cartridge container are recorded and a second area where measurement conditions for using the general-purpose cartridge container are stored, and the operation control means analyzes the measurement conditions read from the recording medium by the information read means, and stores them in the first area when the measurement conditions are measurement conditions related to a measurement using a special-purpose cartridge container and in the second area when the measurement conditions are measurement conditions related to a measurement using a general-purpose cartridge container.

According to this configuration, the present measuring equipment can manage measurement conditions for measurements using the special-purpose cartridge container and measurement conditions for measurements using the general-purpose cartridge container effectively.

In addition, in the above configuration, it is preferable that a specific identification number for each item of the measurement object is given to the special-purpose cartridge container, and when the measurement conditions read from the recording medium by the information read means are measurement conditions related to a measurement using a general-purpose cartridge container, the operation control means gives, as an identification number of a general-purpose cartridge container used for this measurement, an identification number in a range that does not overlap with the identification numbers given to the special-purpose cartridge container in a sequential order, and stores them in the second area.

According to this configuration, measurement conditions for the general-purpose cartridge container can be managed more effectively.

In the aforementioned measuring equipment, it is preferable that all reagents and solvents needed for the measurement are injected separately into the special-purpose cartridge container. The solvents include a dilution for a specimen etc., a solvent used for washing the cartridge container, or the like, for example, such as distilled water, a buffer solution and an organic solvent. According to this configuration, measurements can be conducted even in a situation where a water supply is not present.

In the aforementioned measuring equipment, it is preferable that a waste vessel is disposed in the cartridge container to store waste liquid. According to this configuration, measurements can be conducted even in the environment where waste liquid cannot be treated.

To achieve the above-mentioned object, a first measuring method of the present invention is a measuring method for conducting a measurement using a cartridge container in which a specimen and a reagent are injected separately into a plurality of vessels, and the cartridge container is either a special-purpose cartridge container, which is injected separately in advance with predetermined reagents corresponding to items of a measurement object and sealed with a sealing material on which an information carrier including information relevant to the cartridge container is attached, or a general-purpose cartridge container that does not have the information carrier and is injected separately with reagents by a measurer. The method includes: deciding whether the cartridge container of the measurement object is a special-purpose cartridge container or a general-purpose cartridge container based on whether an information carrier is attached to the cartridge container of the measurement object, and when the cartridge container of the measurement object is a special-purpose cartridge container, conducting a measurement following measurement operation procedures corresponding to the information included in the information carrier, whereas when the cartridge container of the measurement object is a general-purpose cartridge container, outputting an instruction to select items of the measurement object and conducting a measurement following measurement operation procedures corresponding to the selected and input items of the measurement object.

According to this configuration, it has become possible to conduct measurements on specific items of a measurement object by using the special-purpose cartridge container which is injected separately in advance with predetermined reagents or the like as well as on arbitrary items of a measurement object by using the general-purpose cartridge container, in which commercially available reagents etc. are injected separately as needed into an empty cartridge container, so that measuring equipment that is excellent for general purpose use can be provided.

To achieve the above-mentioned object, a second measuring method of the present invention is a measuring method using measuring equipment according to claim 1, and the method includes: separately injecting a predetermined reagent and a specimen into a general-purpose cartridge container, setting the general-purpose cartridge container in the measuring equipment, and selecting and inputting items of a measurement object following an instruction from the measuring equipment to select items of the measurement object.

According to this configuration, in the measuring equipment using a predetermined cartridge container, measurements on arbitrary items of a measurement object can be conducted using a general-purpose cartridge container, in which commercially available reagents etc. are injected separately as needed into an empty cartridge container.

To achieve the above-mentioned object, a first program recording medium of the present invention is a program recording medium that records a control program for directing measuring equipment to execute a measurement using a cartridge container with a plurality of vessels injected separately with a specimen and a reagent. The measuring equipment includes carrier identification means for deciding whether an information carrier is attached to a cartridge container of a measurement object, measurement condition storage means for storing measurement conditions for each item of the measurement object, and measuring means for conducting a measurement according to the measurement conditions. The control program includes: deciding from an output from the carrier identification means whether the cartridge container of the measurement object is a special-purpose cartridge container, which is injected separately in advance with predetermined reagents corresponding to items of the measurement object and sealed with a sealing material on which an information carrier including information relevant to the cartridge container is attached, or a general-purpose cartridge container that does not have the information carrier and is injected separately with reagents by a measurer, and when the cartridge container of the measurement object is a special-purpose cartridge container, conducting a measurement following the measurement conditions read out from the measurement condition storage means based on the information included in the information carrier, whereas when the cartridge container of a measurement object is a general-purpose cartridge container, outputting an instruction to select items of the measurement object and conducting a measurement following the measurement conditions read out from the measurement condition storage means corresponding to the items of the measurement object selected and input based on the output.

The measuring equipment of the present invention can be implemented by directing the CPU etc. to execute the control program recorded in this recording medium. As the recording medium, for example, ROM, a flexible disc, a hard disc, or an arbitrary recording medium such as CD-ROM can be used.

Furthermore, to achieve the above-mentioned object, a second program recording medium of the present invention is a program recording medium that records a control program for directing measurement equipment to store measurement conditions in measurement condition storage means of the measuring equipment. The measuring equipment includes the measurement condition storage means for storing measurement conditions for each item of a measurement object and uses a cartridge container including a plurality of vessels injected separately with a specimen and a reagent. The control program includes: deciding whether the input measurement conditions are measurement conditions related to a measurement using a special-purpose cartridge container, which is injected separately in advance with predetermined reagents corresponding to items of a measurement object and sealed with a sealing material on which an information carrier including information relevant to the cartridge container is attached, or measurement conditions related to a measurement using a general-purpose cartridge container that does not have the information carrier and is injected separately with reagents by a measurer, and based on the decision result, storing the measurement conditions in different areas of the measurement condition storage means according.

The measuring equipment of the present invention can be implemented by directing the CPU etc. to execute the control program recorded in this recording medium. As the recording medium, for example, ROM, a flexible disc, a hard disc, or an arbitrary recording medium such as CD-ROM can be used.

Furthermore, it is preferable that a specific identification number for each item of the measurement object is given to the special-purpose cartridge container, and when the input measurement conditions are measurement conditions related to a measurement using a general-purpose cartridge container, the control program gives, as an identification number of a general-purpose cartridge container used for this measurement, an identification number in a range that does not overlap with the identification numbers given to the special-purpose cartridge container in a sequential order, and stores them in the measurement condition storage means.

In addition, it is preferable in this program that the measurement conditions are recorded in a magnetic recording medium, and the measurement conditions are input from magnetic information read means equipped in the measuring equipment.

BEST MODE FOR CARRYING OUT THE INVENTION

Hereinafter, one embodiment of the present invention will be described with reference to the drawings.

Measuring equipment according to the present embodiment uses a cartridge container injected separately with a necessary liquid reagent etc. to carry out a simplified measurement in such a manner that a sample is prepared by injecting a specimen, for example, human blood or urine etc. into this cartridge container and conducting all the necessary operations for the measurement such as dilution of the specimen, stirring and mixing of the specimen with a reagent or the like inside this cartridge container, transmitting light with a predetermined wavelength through the obtained sample and measuring the absorbency (absorbance) of this light.

Figure 1:
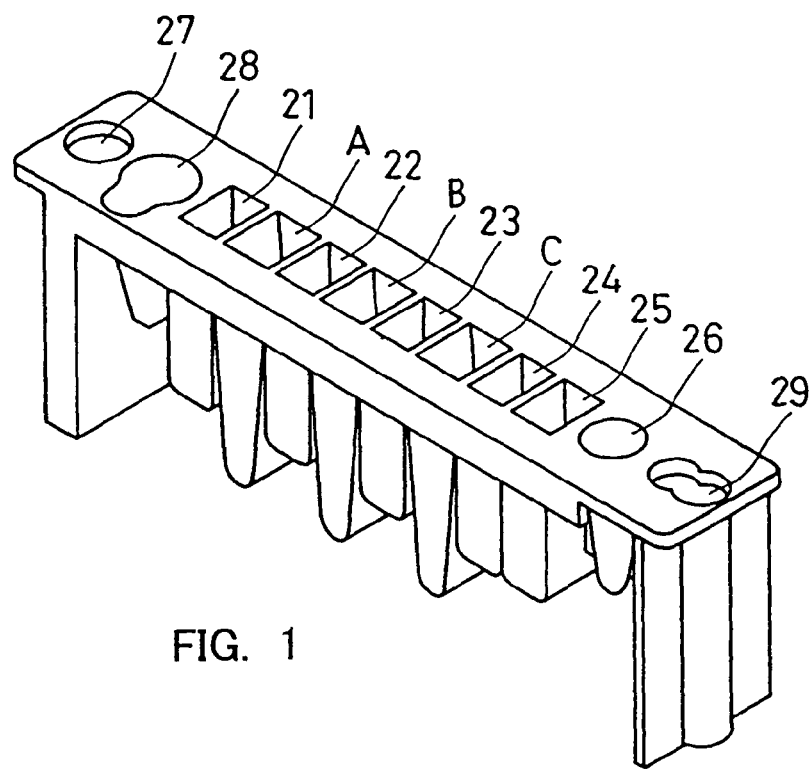
FIG. 1 is a perspective view showing the appearance of a cartridge container (empty cartridge container) used in measuring equipment according to one embodiment of the present invention.
Figure 2:
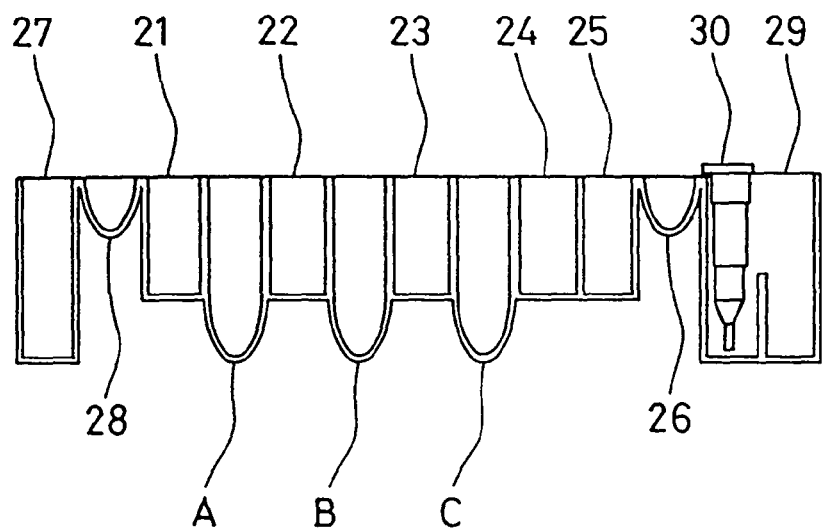
FIG. 2 is a cross-sectional view of the cartridge container.

FIG. 1 is a perspective view showing the configuration of a cartridge container used in the present measuring equipment. FIG. 2 is a cross-sectional view of the cartridge container. As shown in FIG. 1 and FIG. 2, the cartridge container used in the present measuring equipment includes a plurality of wells 21 to 26, a plurality of cells A to C, a specimen container holder 27, a specimen vessel 28 and a waste vessel 29.

The materials for the present cartridge container are not particularly limited, except that at least a transparent material is used for a portion where light is transmitted to measure the absorbance. However, it is preferable to use, for example, a polystyrene resin or the like in view of the production operability as well as the cost.

In preparing a measurement, a specimen is injected into the specimen vessel 28 using a pipette or the like. A specimen that needs to be centrifuged is injected into the specimen container holder 27 and then centrifuged and can be set in this state. A specimen that does not need to be centrifuged (for example, whole blood etc.) can be injected into the specimen vessel 28 as well and measured.

The waste vessel 29 serves for storing waste liquid, but a chip 30 that will be used at the time of measurement is already mounted in the present cartridge container before use. When preparations for a measurement are made, the chip 30 is removed from the waste vessel 29 and mounted on a tip of a nozzle (to be described later) in the measuring equipment, and the chip 30 serves for sucking and draining specimens, samples or the like by operating a sampling pump unit (to be described later) in the measuring equipment.

Corresponding to items of a measurement object, a liquid reagent, a diluted solution, a washing liquid or the like are injected separately into the wells 21 to 26 and the cell A to C. In addition, the present cartridge container is offered to a user of the measuring equipment either in a state in which only the chip 30 is mounted and the wells and the cells etc. are empty without any injection, or, as shown in FIG. 3, in order to serve for measurements of specific items of a measurement object, in a state in which the wells and the cells etc. are injected separately in advance with a predetermined reagent etc. and sealed (hereinafter referred to as a special-purpose cartridge container).

Thus, the user of the measuring equipment can conduct the measurements on specific items of a measurement object by using the special-purpose cartridge container as well as on arbitrary items of the measurement object by using a cartridge container that is prepared by separately injecting commercially available reagents into an empty cartridge container by hand (hereinafter referred to as a general-purpose cartridge container).

Here, the concept "injection by hand" in the present specification is used in contrast to a condition in which reagents or the like are injected separately in advance into a special-purpose cartridge container during the manufacturing process of this package and refers to the act of separately injecting reagents into a cartridge container after the user of the measuring equipment obtained the cartridge container, and it is not important to distinguish whether the act of injection itself is conducted by human hand or by machine.

Figure 3:
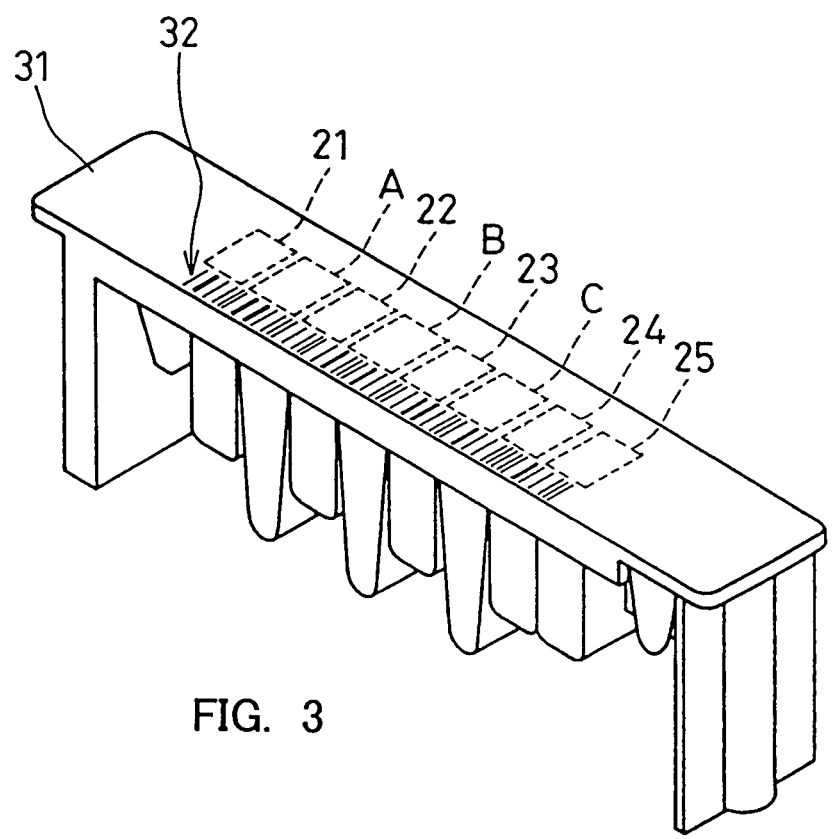
FIG. 3 is a perspective view showing the appearance of a special-purpose cartridge container used in the measuring equipment.

As shown in FIG. 3, when the present cartridge container is offered in the form of a special-purpose cartridge container that is injected separately in advance with predetermined reagents etc., the reagents etc. are injected separately, and then the container is sealed by attaching a seal 31 on the upper surface of the package. On the surface of this seal 31, a bar code 32 is attached beside the openings of the wells 21 to 26 and the cells A to C. The bar code 32 includes, as information related to this special-purpose cartridge container, information such as an item number of the measurement object, a cartridge container number, an expiration date and so forth. In addition, as far as the amount of information is within a recordable limit of the bar code 32, a lot number of this cartridge container or other information may be included.

On the other hand, the empty cartridge container is shipped, as shown in FIG. 1, without being sealed and without even a bar code attached. The manufacturer of the present measuring equipment provides the user of the measuring equipment with a separate injection procedural manual in which the manual separate injection procedures are described for each item of the measurement object required by the user, in other words, which reagent should be injected in which amount into which well (or cell) of the empty cartridge container, as well as with a magnetic card recording the measurement operation procedures etc. for the measuring equipment when such a package containing commercial reagents injected separately by hand (a general-purpose cartridge container) is set. In addition, as needed, the measurement operation procedures for the measuring equipment in the case of using a special-purpose cartridge container also are recorded in the magnetic card, and the magnetic card is offered from the manufacturer of the measuring equipment to the user.

When the user purchases the measuring equipment or needs to add new items of the measurement object and so on, the user is provided with a magnetic card concerning the necessary items of the measurement object. This magnetic card can be read by a magnetic card reader (to be described later) in the measuring equipment, so that the measurement conditions for these items of the measurement object are registered in the measuring equipment. In addition, the measurement conditions for the special-purpose cartridge container may be registered in advance in the measuring equipment at the time of shipment, and the magnetic card may be attached to the apparatus as backup.

Figure 4:
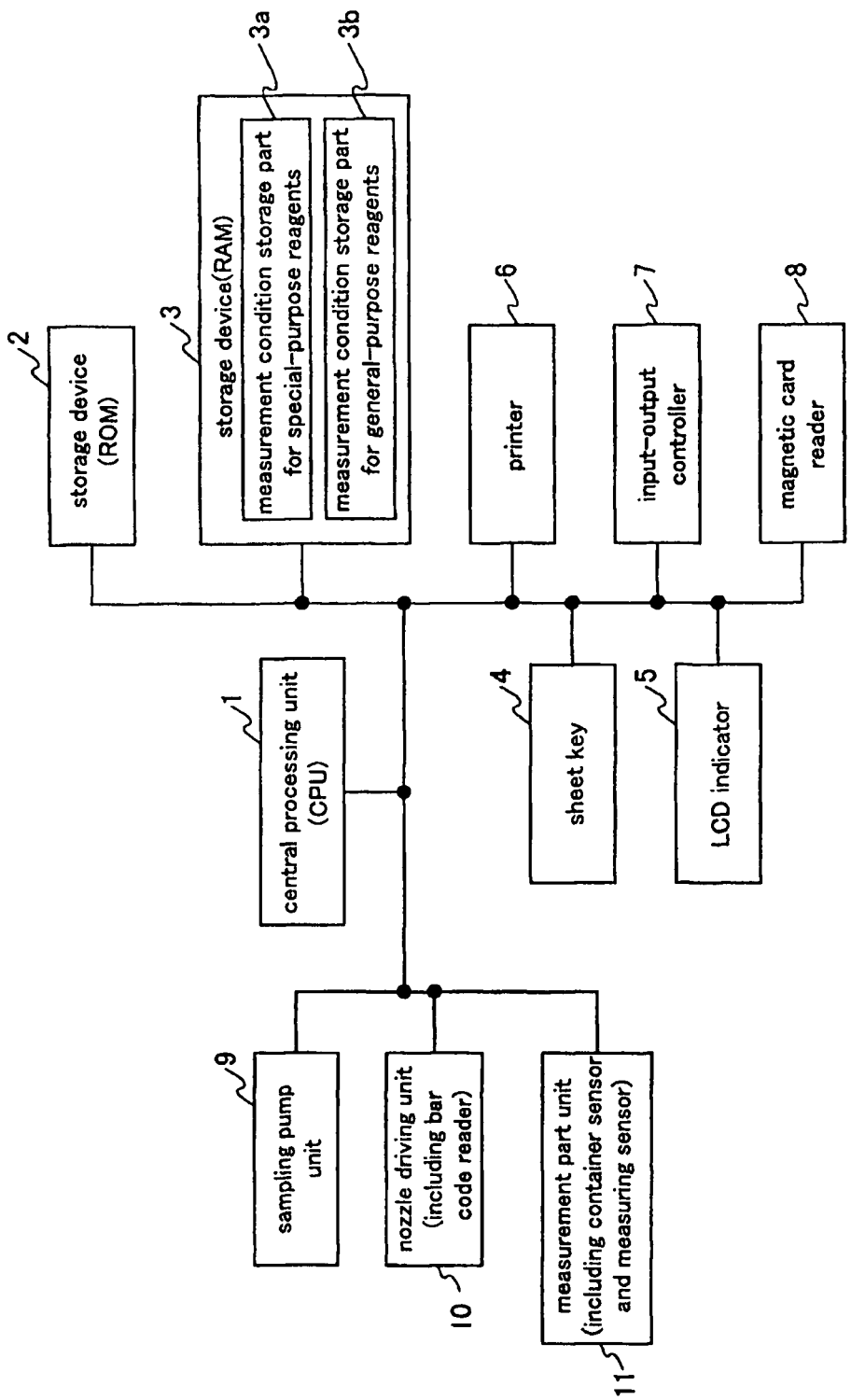
FIG. 4 is a block diagram showing the configuration of the measuring equipment.

Here, the configuration of the measuring equipment according to the present embodiment will be explained. FIG. 4 is a block diagram showing the configuration of the present measuring equipment. The present measuring equipment includes a central processing unit (CPU) 1, a ROM 2, a RAM 3, a sheet key 4 used by a user to input operator guidance etc., an LCD indicator 5 made of a liquid crystal display, a printer 6 for printing out measurement results etc., an input-output controller 7 implemented with a communication interface, for example, RS-232C etc., a magnetic card reader 8, a sampling pump unit 9, a nozzle driving unit 10 and a measurement part unit 11.

The sampling pump unit 9 has a pump and controls sucking and draining of specimens, reagents etc. under the control of the CPU 1 by operating this pump via the chip 30 to be mounted on the tip of the nozzle of the nozzle driving unit 10. The nozzle driving unit 10 controls the operation of the aforementioned nozzle on the cartridge container under the control of the CPU 1.

The nozzle of the nozzle driving unit 10 also has the function of opening the seal 31 when the special-purpose cartridge container is set in the present measuring equipment. This nozzle is made, for example, of stainless steel or the like and is capable of piercing the seal 31 to make a hole. Thus, after holes are made in apertures such as wells or cells required for the measurement, the nozzle tip is inserted into the chip 30 that is mounted in the waste vessel 29 so that the chip 30 is placed on the nozzle.

The CPU 1 transfers reagents etc. injected separately into the cartridge container to another well or cell, for example, by controlling the operation of the sampling pump unit 9 and that of the nozzle driving unit 10 as follows. First, the CPU 1 shifts the nozzle of the nozzle driving unit 10 horizontally on the upper surface of the cartridge container and stops the nozzle temporarily above an intended well or cell.

Next, the nozzle is sent down from above this well or cell, so that the tip of the chip 30 attached on the nozzle tip reaches the liquid surface inside this well or the cell. Thereafter, by operating the sampling pump unit 9 to conduct sucking, the reagent etc. injected separately inside this well or cell is sucked into the chip 30.

In addition, the nozzle is sent up above this well or cell and shifted horizontally to be above another well or cell. Then, the nozzle is sent down from above this well or cell, and then the sampling pump unit 9 is operated to conduct draining. Thus, the reagent etc. in a certain well or cell is transferred to a different well or cell.

The present measuring equipment thus carries out dilution of a specimen or mixing of the specimen with reagents to create samples for measurements by performing a transfer of a predetermined amount of specimen, reagent, a dilution solution or the like from a certain well or cell to another well or cell following the procedures corresponding to the items of the measurement object. Furthermore, any one of the wells can be injected separately with a washing solution, and when the operation of sucking the washing solution from this well into the chip 30 and draining it to the waste vessel 29 is conducted for several times at the time between a certain reagent etc. was transferred and another reagent etc. is to be transferred, the chip 30 can be washed, so that it is possible to prevent an unwanted reagent etc. from mixing therein.

Furthermore, the nozzle driving unit 10 is equipped with a bar code reader for reading the bar code 32 of the cartridge container (the special-purpose cartridge container). The measurement part unit 11 not only has the mechanism of fixing a cartridge container but also includes a container sensor for identifying whether a cartridge container is set in this mechanism and a measuring sensor for detecting the items of the measurement object. In addition, as the aforementioned measuring sensor, a spectrophotometer or the like can be used to determine the absorbance of a sample using light with a predetermined wavelength.

Hereinafter, the operation of the present measuring equipment will be described with reference to the flow charts of FIG. 5 to FIG. 9.

Figure 5:
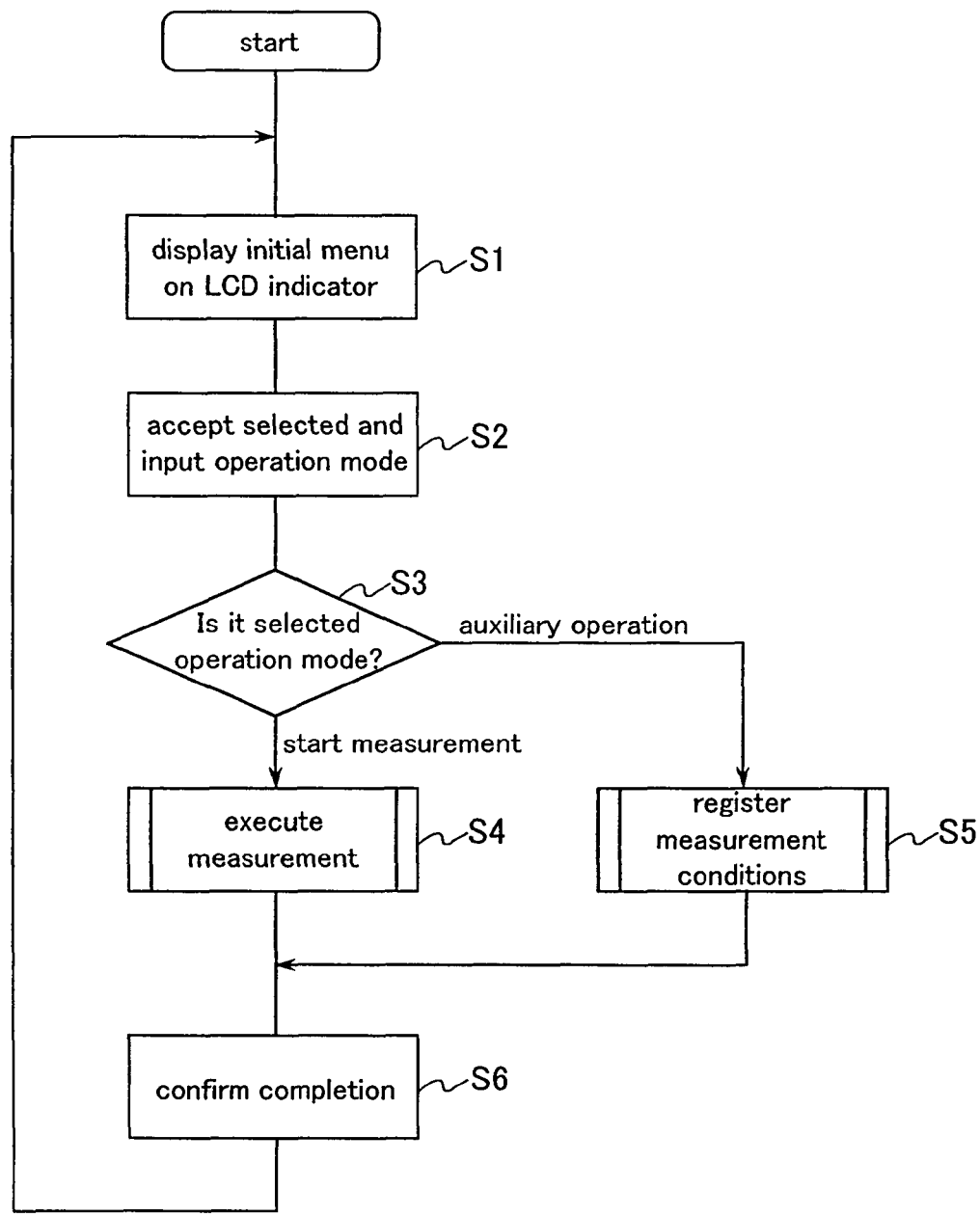
FIG. 5 is a flow chart showing the flow of main processing in the measuring equipment.

FIG. 5 is a flow chart showing the flow of main processing in the measuring equipment. As shown in FIG. 5, the CPU 1 in the present measuring equipment displays an initial menu on the LCD indicator 5 from which an operator selects the operation mode of the measuring equipment such as "start measurement" and "auxiliary operation" (Step S1).

When the operator selects his desired operation mode and performs a key entry from the sheet key 4, the CPU 1 accepts this key entry (Step S2) and operates in the operation mode selected by the operator (Step S3 to S5), and when the processes in the respective operation modes are completed, a message is displayed for the operator to confirm that the operation is completed. After receiving an authentication entry for this message (Step S6), the CPU 1 returns to Step S1 and displays the initial menu on the LCD indicator 5.

In addition, as an example of the operation mode for the "auxiliary operation", FIG. 5 only shows a "registration of measurement conditions (Step S5)" in which the measurement conditions are registered in the measuring equipment using the aforementioned magnetic card. However, as operations included in the "auxiliary operation" other than this registration of measurement conditions, a deletion of the registered measurement conditions etc. is conceivable.

Figure 6:
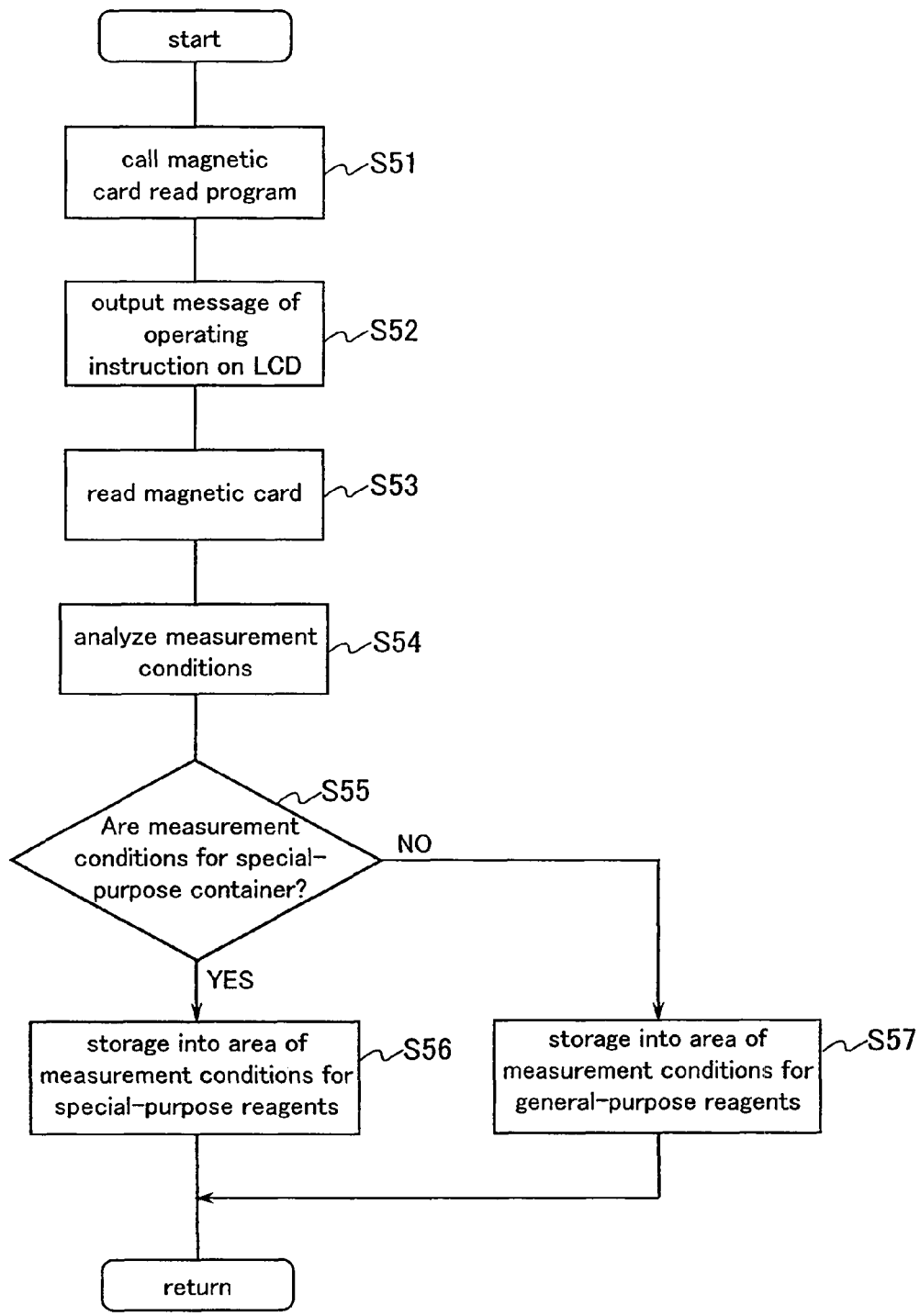
FIG. 6 is a flow chart showing the process of Step S5 in FIG. 5 in detail.

Here, the process of the "registration of measurement conditions" in Step S5 will be described in more detail with reference to the flow chart of FIG. 6. This process is performed for registering measurement conditions for each item of a measurement object using a magnetic card provided by the manufacturer when a user of the present measuring equipment purchases the measuring equipment or needs to add new items of the measurement object.

The CPU 1 first reads out a magnetic card read program from the ROM 2 (Step S51). The processes to be followed are performed in that the CPU 1 operates following this magnetic card read program. After completing the readout of the program, the CPU 1 displays a message on the LCD indicator 5 instructing the insertion of the magnetic card into the magnetic card reader 8 (Step S52). When the operator follows this message and passes the magnetic card containing measurement conditions through the magnetic card reader 8, the measurement conditions recorded in the magnetic card are input to the present measuring equipment (Step S53).

The CPU 1 analyzes the information input from the magnetic card reader 8 (Step S54). Items to be input as the measurement conditions are the item names of the measurement object, the item numbers of the measurement object, the cartridge container number, the expiration date, the operating procedures (measurement operation procedures) for the sampling pump unit 9, the nozzle driving unit 10 and so forth and the method for calculating the results.

With respect to the aforementioned item numbers of the measurement object recorded in the magnetic card, a specific number is defined for each item name of the measurement object. With respect to the cartridge container number, a specific number is defined for each item of the measurement object with respect to the measurement conditions using a special-purpose cartridge container. However, with respect to the measurement conditions using a general-purpose cartridge container, a null value is given as the cartridge container number regardless of the items of the measurement object.

Therefore, when the information input from the magnetic card reader 8 is analyzed, the CPU 1 decides whether the input measurement conditions are targeted for a special-purpose container or for a general-purpose cartridge container based on whether the cartridge container number is a significant number or a null value (Step S55).

As a result of this decision, when it involves measurement conditions for a special-purpose cartridge containers (YES in Step S55), the measurement conditions input from the magnetic card reader 8 are stored as they are in an area (a measurement condition storage part for special-purpose reagents 3*a*) of the RAM 3 where measurement conditions concerning measurements using a special-purpose cartridge container are to be stored (Step S56).

On the other hand, when it involves measurement conditions for a general-purpose cartridge container (NO in Step S55), the cartridge container number indicated as a null value is replaced with an appropriate cartridge container number within the measurement conditions input from the magnetic card reader 8 and then stored in an area (a measurement condition storage part for general-purpose reagents 3*b*) where measurement conditions concerning measurements using a general-purpose cartridge container are to be stored (Step S57). This replacement of the cartridge container number is performed within a range of numbers reserved for a general-purpose cartridge container such that this number can be distinguished from the special-purpose cartridge container number and that the numbers for general-purpose cartridge containers do not overlap with each other. For example, when the numbers for special-purpose cartridge containers are determined in a range of 1 to 60, the numbers from 70 and after will be allocated in a sequential order for general-purpose cartridge containers.

When the process of Step S56 or Step S57 is completed, the CPU 1 returns the control to main processing (return).

According to the processes of Step S51 to Step S57 described above, the measurement conditions are stored in the RAM 3 of the measuring equipment. In addition, since the RAM 3 is nonvolatile memory, there is no need to register the once stored measurement conditions again as long as the contents of the measurement conditions do not require any change.

Next, the process of the "execute measurement" in Step S4 shown in FIG. 5 will be described in detail with reference to the flow chart of FIG. 7. This process is a process for performing an actual measurement by using a special-purpose cartridge container or a cartridge container that is prepared by separately injecting commercially available reagents (general-purpose reagents) into an empty cartridge container by hand.

Before starting a measurement, the operator prepares a specimen and a cartridge container that is injected separately with reagents corresponding to the items of the measurement object to be measured from this specimen. Depending on the items of the measurement object, this cartridge container may be a special-purpose cartridge container as well as a cartridge container that is prepared by separately injecting general-purpose reagents into an empty cartridge container by hand according to the aforementioned separate injection procedural manual. Here, the above-mentioned specimen is, for example, a body fluid or the like such as human blood and urine, and is injected separately into the specimen vessel 28 of the cartridge container before starting the measurement.

As already described, the measuring equipment displays an initial menu on the LCD indicator 5 from which the operator selects the operation mode of the measuring equipment such as "start measurement" and "auxiliary operation" (Step S1 in FIG. 5). Here, when the operator selects the "start measurement" from the initial menu and performs a key entry from the sheet key 4, the measurement execution process in Step S4 is initiated.

Figure 7:
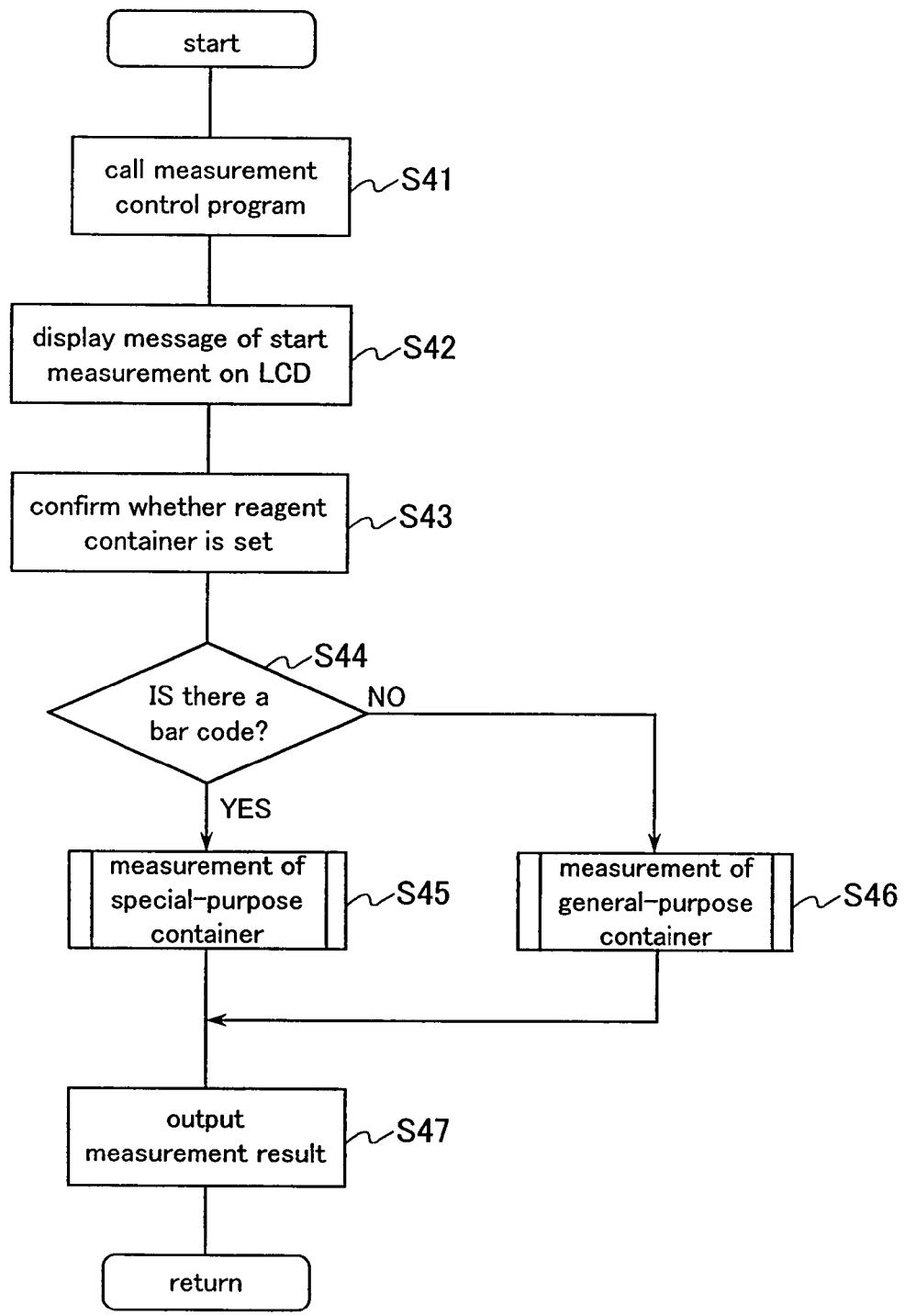
FIG. 7 is a flow chart showing the process of Step S4 in FIG. 5 in detail.

As shown in FIG. 7, the CPU 1 first calls the measurement control program that controls the measurement operation from the ROM 2 (Step S41). The processes to be followed are performed in that the CPU 1 operates following this measurement control program. After completing the readout of the program, the CPU 1 displays a message "start measurement" on the LCD indicator 5 (Step S42).

Here, the operator confirms the contents displayed on the LCD indicator 5 and sets a cartridge container (a special-purpose cartridge container or a cartridge container prepared by separately injecting general-purpose reagents into an empty cartridge container) into the measurement part unit 11. The CPU 1 recognizes that the cartridge container was set in the measurement part unit 11 based on a signal of ON/OFF from the cartridge container sensor mounted on the measurement part unit 11 (Step S43). At this stage, in order to prevent a false recognition from occurring, the CPU 1 confirms the sensor signal in the measurement part unit 11 at least twice at a constant interval to verify whether the cartridge container is set correctly.

After confirming that the cartridge container is set, the CPU 1 sends a control instruction to the nozzle driving unit 10 and reads the bar code information of the cartridge container being set in the measurement part unit 11 with a bar code reader mounted on the nozzle driving unit (Step S44).

In the case where the cartridge container being set is a special-purpose cartridge container, the bar code 32 is read, so that the decision result in Step S44 becomes YES, and it proceeds to Step S45 to carry out a measurement using the special-purpose cartridge container. On the other hand, in the case where the cartridge container being set is the one prepared by separately injecting general reagents into an empty cartridge container, since there is no bar code, the decision result in Step S44 becomes NO, and it proceeds to Step S46 to carry out a measurement following the measurement procedures for a general-purpose cartridge container. In addition, the processes in Step S45 and Step S46 will be described later in detail.

When the process of Step S45 or Step S46 is completed, the CPU 1 outputs the measurement result obtained by the process of Step S45 or Step S46 to the LCD indicator 5, the printer 6 and the input-output control part 7 (Step S47).

Then, when the operator removes the used cartridge container from the measurement part unit 11, the CPU 1 recognizes that the cartridge container was removed based on a sensor signal from the measurement part unit 11 and returns to the main processing shown in the flow chart of FIG. 5.

Figure 8:
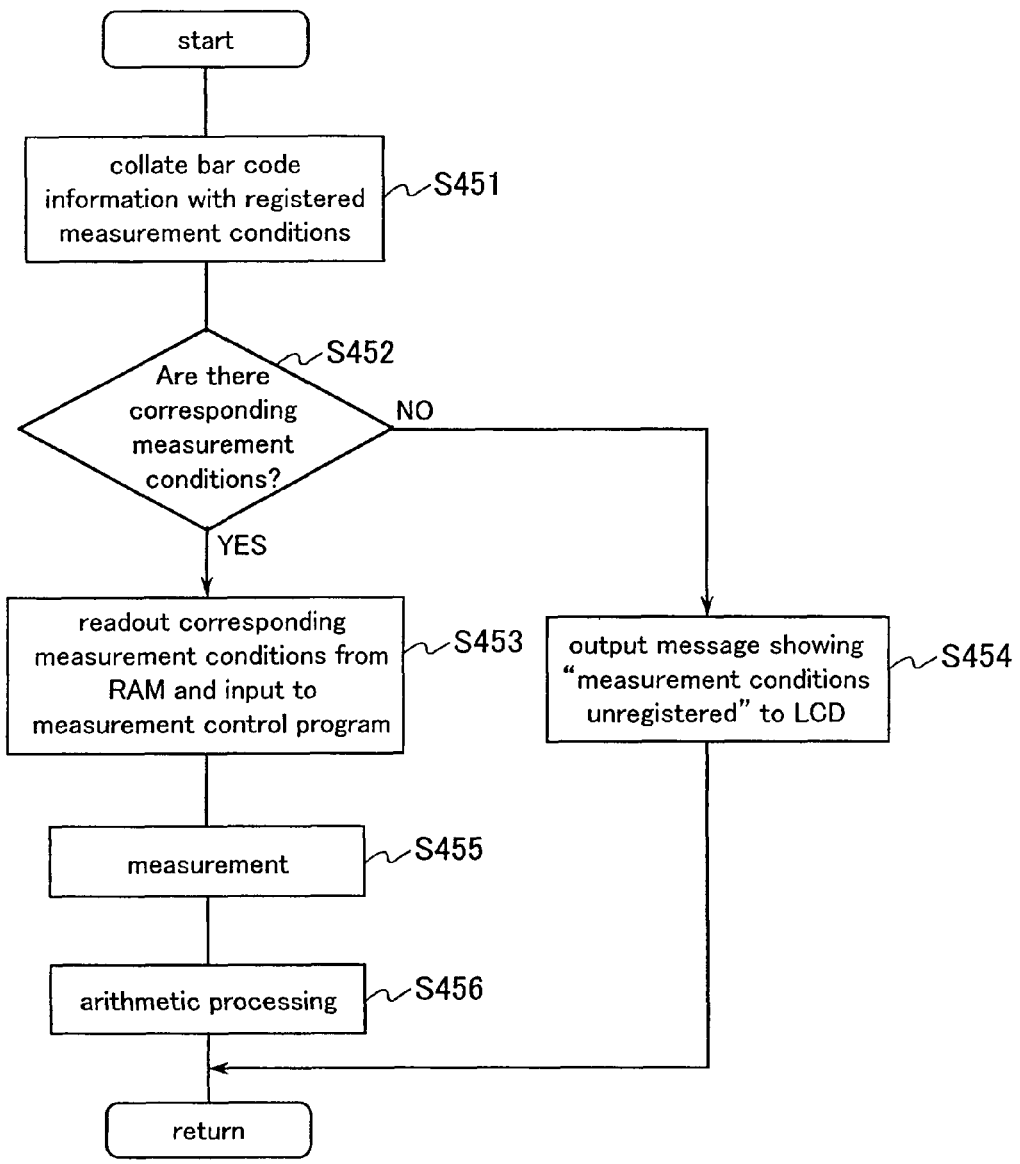
FIG. 8 is a flow chart showing the process of Step S45 in FIG. 7 in detail.

Here, the process in Step S45 mentioned above, which is performed when the cartridge container being set is a special-purpose cartridge container, will be described in detail with reference to the flow chart of FIG. 8.

The CPU 1 collates the bar code information being read by the nozzle driving unit 10 in Step S44 shown in FIG. 7 with the information stored in the RAM 3 (Step S451). In other words, as already described, the information such as the item numbers of the measurement object, the cartridge container number, the expiration date and so forth are recorded in the bar code 32 attached on the special-purpose cartridge container, so that the CPU 1 uses the item numbers of the measurement object and the expiration date recorded in the bar code 32 as the retrieval key for retrieving the measurement condition storage part for special-purpose reagents 3a in the RAM 3.

As a result, when the measurement conditions including the item numbers of the measurement object and the expiration data that correspond to the retrieval key are stored in the measurement condition storage part for special-purpose reagents 3a of the RAM 3 (YES in Step S452), the CPU 1 reads out the item names of the measurement object and the measurement operation procedures from these measurement conditions and performs a parameter input to the measurement control program that has already been read out in Step S41 shown in FIG. 7 (Step S453).

Then, the CPU 1 displays a message on the LCD indicator 5 indicating that the measurement operation has been initiated automatically and conducts the measurement by controlling the sampling pump unit 9 and the nozzle driving unit 10 following the above-mentioned measurement control program (Step S455). When the measurement is completed, an arithmetic processing of the measurement result is conducted as needed (Step S456), and the CPU 1 returns to the process shown in the flow chart of FIG. 7.

On the other hand, as a result of the collation in Step S451, when the measurement conditions including the item numbers of the measurement object and the expiration data that correspond to the retrieval key are not stored in the RAM 3 (NO in Step S452), the CPU 1 displays a message on the LCD indicator 5 informing that the measurement conditions of the special-purpose cartridge container being set are unregistered (Step S454), and the CPU 1 returns to the process shown in the flow chart of FIG. 7.

Figure 9:
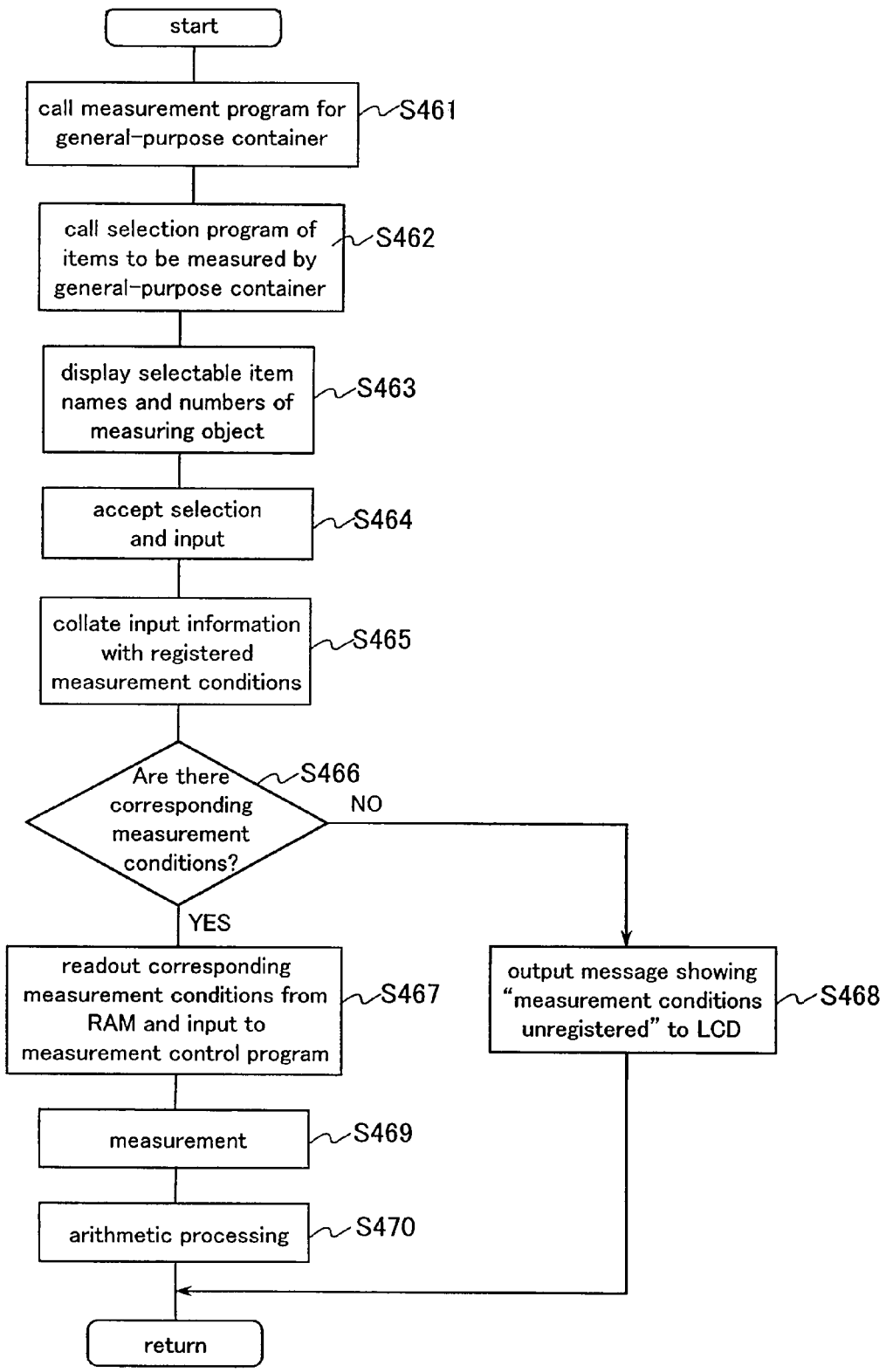
FIG. 9 is a flow chart showing the process of Step S46 in FIG. 7 in detail.

Next, the process in Step S46 mentioned above, which is performed when the cartridge container being set is a general-purpose cartridge container that is prepared by separately injecting general-purpose reagents into an empty cartridge container by hand, will be described in detail with reference to the flow chart of FIG. 9.

The CPU 1 first reads out the program for controlling the measurement operation in the case of using a general-purpose cartridge container from the ROM 2 (Step S461). The processes to be followed are performed in that the CPU 1 operates following this program.

Next, the CPU 1 reads out the selection program that allows the operator to select and input the items of the measurement object from the ROM 2. Based on this selection program, the CPU 1 displays the item names of the measurement object and the item numbers of the measurement object that can be selected on the LCD indicator 5 (Step S463).

The operator looks at the display on the LCD indicator 5 and conducts a key entry to select the desired item names of the measurement object from the sheet key 4. The CPU 1 accepts this key entry (Step S464) and collates the selected item names of the measurement object with the information stored in the measurement condition storage part for general-purpose reagents 3b of the RAMS 3 (Step S465).

As a result of the collation, when the measurement conditions including the information corresponding to the item names of the measurement object selected by the key entry (the item numbers of the measurement object and the cartridge container number) are stored in the measurement condition storage part for general-purpose reagents 3b of the RAM 3 (YES in Step S466), the CPU 1 reads out these item names of the measurement object and the measurement operation procedures from the RAM 3 and performs a parameter input to the measurement program that has already been read out in Step S461 to initiate the measurement operation (Step S467). At the same time, the CPU 1 at this stage displays on the LCD indicator 5 that the measurement operation has been initiated.

When the measurement operation starts, the CPU 1 conducts a predetermined measurement operation by controlling the sampling pump unit 9 and the nozzle driving unit 10 following the measurement operation procedures that was read out from the RAM 3 (Step S469). When the measurement is completed, an arithmetic processing of the measurement result is conducted as needed (Step S470), and the CPU 1 returns to the process shown in the flow chart of FIG. 7.

As described above, when the cartridge container was set in the measurement part unit 11, the present measuring equipment decides whether this cartridge container has a bar code using a bar code reader mounted on the nozzle driving unit 10. As a result, when the bar code can be read, the measurement conditions for a special-purpose cartridge container are read out from the RAM 3 to conduct a measurement, whereas when the bar code can not be read, the measurement conditions for a general-purpose cartridge container are read out to conduct a measurement.

According to this configuration, it has become possible not only to measure specific items of a measurement object using a special-purpose cartridge container injected separately in advance with predetermined reagents etc. but also to measure arbitrary items of the measurement object by using a cartridge container prepared by separately injecting commercial reagents etc. by hand into an empty cartridge container. As a result, highly versatile measuring equipment can be implemented.

EXAMPLES

Hereinafter, more specific examples in the embodiment of the present invention will be described, but the present invention is not limited thereto.

Example 1

In the present example, a prototype of the measuring equipment according to the present invention was built, and a cartridge container prepared by separately injecting general-purpose reagents into an empty cartridge container by hand was used to conduct a rheumatoid factor (RF) immunological nephelometric measurement. Then, these measurement results were compared with the equivalent measurement results obtained by a conventional automatic analyzer (manufactured by Nihon Denshi Co., Ltd.: Biochemical Automatic Analyzer JCA-BM8 (product name)). In addition, the aforementioned measuring equipment used in the present example was implemented by using conventional measuring equipment with the same hardware configuration as that shown in FIG. 4 in the aforementioned embodiment of the present invention and loading a program for performing the processes shown in FIG. 5 to FIG. 9 into its CPU. The measurements were carried out as follows:

(1) Various parameters such as a factor of dilution in the RF-Latex x1 "Seiken" (product name, manufactured by Denka Seiken Co.), which is commercially available as a special-purpose reagent kit, was determined for JCA-BM8. The mixing ratio was determined to be 140 micro liters (μL) for the buffer solution, 47 μL for Latex and 4 μL for the specimen (blood plasma). In addition, the dilution rate of the specimen was determined to be fivefold, and the amount of the diluted specimen used was determined to be 20 μL. In addition, the measuring wavelength of JCA-BM8 is 658 nm. Other detailed settings were determined following the instructions from the manufacturer.

Figure 11:
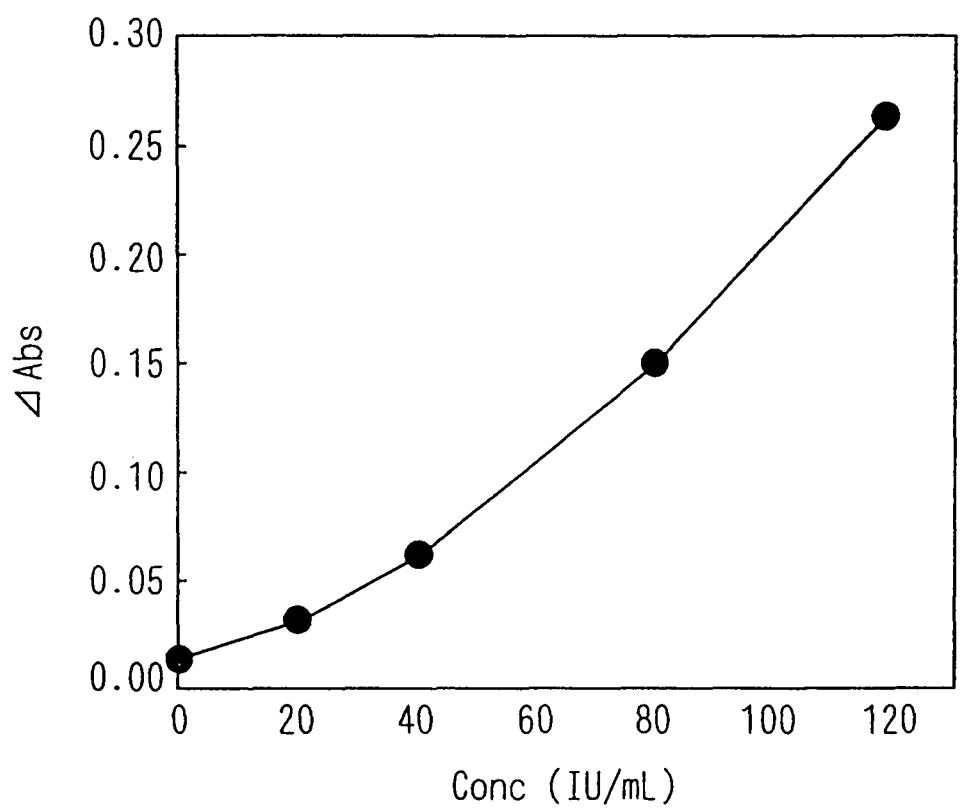
FIG. 11 is a graph showing a calibration curve in a conventional automatic analyzer.

(2) The RF standard solution (product name, manufactured by Denka Seiken Co.) included in the aforementioned special-purpose reagent kit was dissolved as instructed by the manufacturer to conduct a measurement for preparing a calibration curve using JCA-BM8. The results are shown in Table 1 and FIG. 11.

TABLE 1

| Standard Solution (IU/ml) | Measurement-1 | Measurement-2 | Average |
|---|---|---|---|
| 0 | 0.0134 | 0.0136 | 0.01350 |
| 20 | 0.0319 | 0.0315 | 0.03170 |
| 40 | 0.0609 | 0.0622 | 0.06155 |
| 80 | 0.1506 | 0.1502 | 0.15040 |
| 120 | 0.2656 | 0.2634 | 0.26450 |

(3) The measurement of the aforementioned specimen was conducted using JCA-BM8, and a RF concentration of the specimen was obtained from the calibration curve prepared in (2). The results are shown later in Table 3.

(4) Corresponding to the parameters of JCA-BM8, parameters for the present measuring equipment were prepared. At this stage, the mixing ratio for the buffer, Latex, and the specimen was determined to be 140:47:4 just like for JCA-BM8. The mixing ratio was 140 μL for the buffer solution, 47 μL for Latex, and 4 μL for the specimen.

In this mixing ratio, when the dilution rate of the specimen was determined to be twentyfold in order to conduct a whole blood measurement and a hematocrit correction at the time of the whole blood measurement more easily, the amount of diluted specimen used becomes 80 μL. In addition, when a whole blood measurement is not conducted, it is also possible to inject separately 20 μL of the specimen diluted fivefold as in (1). In the present example, the amount of separate injection for each reagent was reset to 60% of the aforementioned amounts, that is, 84 μL for the buffer solution, 28.2 μL for Latex and 2.4 μL for the specimen.

In addition, the measuring wavelength of the present measuring equipment is 660 nm, while the measuring wavelength of JCA-BM8 is 658 nm. However, since the measuring wavelength for these reagents is set in a range of 550 to 660 nm, a difference in their measuring wavelength does not affect the measurement results.

(5) According to the separate injection procedural manual, reagents were injected separately into an empty cartridge container by hand. In this separate injection procedural manual, the amounts of the respective reagents to be injected separately into each well of the empty cartridge container (See FIG. 2) are designated as follows:

| well 22: | Hb measuring reagent | 300 μL |
| well 23: | physiological salt solution | 420 μL |
| well 24: | buffer solution | 330 μL |
| well 25: | distilled water | 380 μL |
| well 26: | Latex | 50 μL |

In the present example, a physiological salt solution is injected separately into the well 23 and used for the purpose of diluting the whole blood twentyfold in order to measure the whole blood that was hemolyzed in advance by freezing and thawing. When the whole blood used is not hemolyzed, a solution that causes hemolysis (for example, saponin solution) is injected separately herein. Furthermore, in the case where there is a specimen diluent designated by the manufacturer who supplies the reagent, it is preferable to inject this specimen diluent separately herein and to conduct the dilution of the specimen at a dilution rate designated by the manufacturer. In addition, in the case where a whole blood measurement is not conducted and even a dilution of the specimen is not necessary, the reagents do not need to be injected separately into the well 23 and the parameters related thereto become unnecessary.

(6) The measurement operation procedures for the cartridge container into which the reagents were injected separately according to (5) described above were recorded in a magnetic card, and this magnetic card was read by the magnetic card reader 9, as described above, so that the measurement operation procedures for this cartridge container were registered in the present measuring equipment. In addition, the sequences for the measurement operation procedures are shown as (a) to (m) below.

(a) 95 μL physiological salt solution is transferred two times from the well 23 to the well 21, so that a total of 190 μL physiological salt solution is injected separately into the well 21.

(b) 84 μL buffer solution is transferred from the well 24 to the cell B.

(c) 77 μL Hb measuring reagent is transferred two times from the well 22 to the cell A, so that a total of 154 μL Hb measuring reagent is injected separately into the cell A.

(d) After 110 μL of sucking and draining is conducted two times with the physiological salt solution left in the well 23, the chip 30 is washed by transferring 50 μL distilled water of the well 25 into the waste vessel 29.

(e) 10 μL specimen in the specimen vessel 28 is transferred to the well 21, and 110 μL of sucking and draining is conducted five times inside the well 21 to stir and mix the liquid inside the well 21.

(f) After 110 μL of sucking and draining is conducted two times with the physiological salt solution left in the well 23, the chip 30 is washed by transferring 50 μL distilled water of the well 25 into the waste vessel 29.

(g) 28 μL diluted specimen in the well 21 is transferred to the cell A, and 110 μL of sucking and draining is conducted five times inside the cell A to stir and mix the liquid inside the cell A.

(h) A change in the absorbance of the cell A is detected, and the Hb concentration is measured.

(i) After 110 μL of sucking and draining is conducted two times with the buffer solution left in the well 24, the chip 30 is washed by transferring 50 μL distilled water of the well 25 into the waste vessel 29.

(j) 48 μL diluted specimen in the well 21 is transferred to the cell B, and 85 μL of sucking and draining is conducted five times inside the cell B to stir and mix the liquid inside the cell B.

(k) After 110 μL of sucking and draining is conducted two times with the distilled water left in the well 25, the chip 30 is washed by transferring 110 μL distilled water of the well 25 into the waste vessel 29.

(l) 28.2 μL Latex in the well 26 is injected separately into the cell B, and 110 μL of sucking and draining is conducted three times to stir and mix the liquid inside the cell B.

(m) A change in the absorbance of the cell B is detected, and the RF concentration is measured.

Figure 10:
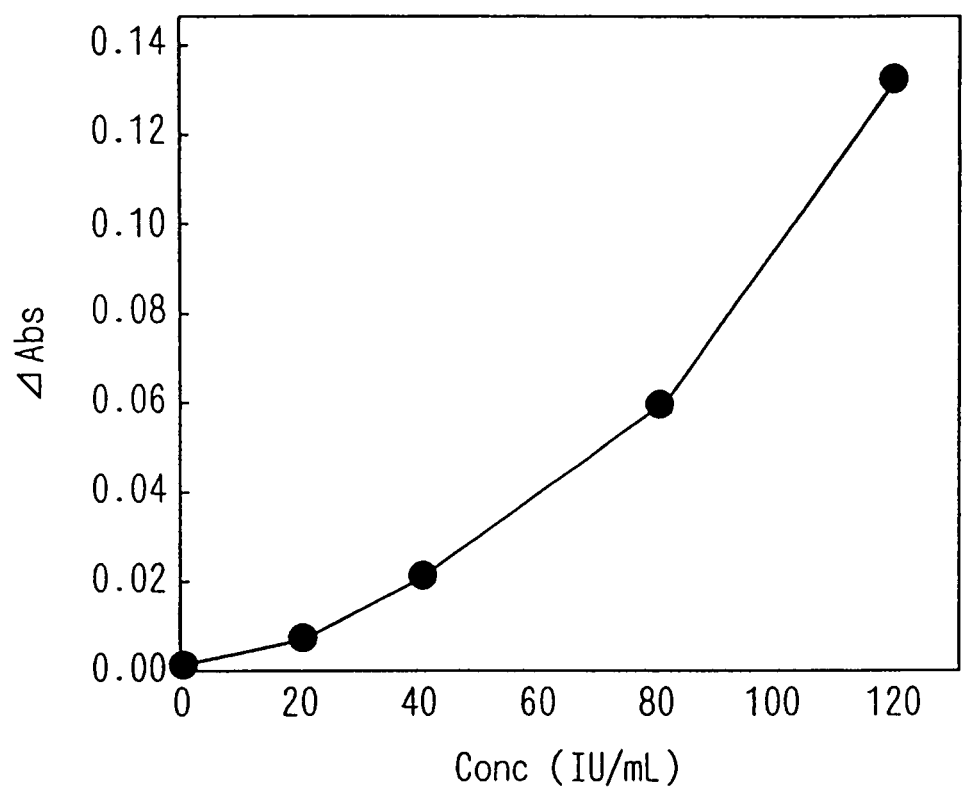
FIG. 10 is a graph showing a calibration curve in measuring equipment according to one example of the present invention.

(7) To prepare a calibration curve, the RF standard solution of (2) was injected separately into the specimen vessel 28 of the cartridge container into which the reagents had been injected separately by hand as shown in above (5), and measurements were conducted with the present measuring equipment and thus changes in the absorbance (delta Abs) were obtained. The results are shown in Table 2 and FIG. 10. In addition, in the present example, the measurements were conducted two times in each case to prepare the calibration curve for the present measuring equipment based on their average values, but the number of measurements can be changed depending on the time required for the measurement, the amounts of reagents, or the measuring accuracy required and so forth.

TABLE 2

| Standard Solution (IU/ml) | Measurement-1 | Measurement-2 | Average |
| --- | --- | --- | --- |
| 0 | 0.0012 | 0.0018 | 0.00150 |
| 20 | 0.0079 | 0.0070 | 0.00745 |
| 40 | 0.0220 | 0.0212 | 0.02160 |
| 80 | 0.0594 | 0.0623 | 0.06085 |
| 120 | 0.1329 | 0.1314 | 0.13215 |

(8) The delta Abs obtained in above (7) was input to the present measuring equipment to prepare the calibration curve. This entry was done by a magnetic card. In addition, when the calibration curve is not used, the measurement results by the delta Abs can be obtained.

(9) The same specimen as that in (3) is injected separately into the specimen vessel 28 of the cartridge container into which the reagents had been injected separately by hand as shown in above (5), and the cartridge container was set in the present measuring equipment to conduct measurements, and the RF concentration was obtained.

(10) The measurement results obtained respectively from JCA-BM8 and the present measuring equipment were compared with each other. The results are shown in Table 3. Although a divergence of 7.4% at most was observed, by taking the performance (CV=8% or less, n=10) of the reagents used this time into consideration, the measuring equipment is adequate for practical use. The measurements conducted by using the cartridge container prepared by separately injecting general-purpose reagents into an empty cartridge container for the present measuring equipment proved that the measurement results equivalent to those by the conventional automatic analyzer can be obtained.

TABLE 3

| Specimen | JCA-BM8 | present reagent measuring equipment | divergence (%) |
| --- | --- | --- | --- |
| blood plasma-1 | 15 | 16 | 6.7 |
| blood plasma-2 | 18 | 18 | 0.0 |
| blood plasma-3 | 27 | 29 | 7.4 |
| blood plasma-4 | 30 | 29 | −3.3 |
| blood plasma-5 | 49 | 50 | 2.0 |

TABLE 3-continued

| Specimen | JCA-BM8 | present reagent measuring equipment | divergence (%) |
|---|---|---|---|
| blood plasma-6 | 54 | 56 | 3.7 |
| blood plasma-7 | 86 | 90 | 4.7 |

Example 2

Measurements were conducted for specimens of whole blood in the present measuring equipment.

Two specimens of whole blood having different RF concentrations (EDTA, 2K blood added) were prepared. Then, the specimens were partially centrifuged to obtain blood plasmas, and at the same time, the rest was hemolyzed by freezing and thawing as whole blood samples.

As in Example 1, a cartridge container is prepared by separately injecting general-purpose reagents into an empty cartridge container to conduct the measurements of the blood plasmas and the whole blood. The measurement values of the RF concentrations in the obtained whole blood were subject to hematocrit conversion by determining the hematocrit values (%) from the Hb concentration obtained simultaneously (measurement values of RF in whole blood/(1-hematocrit value(%)/100). This hematocrit conversion is conducted as an "arithmetic processing" shown in Step S456 of FIG. 8 and in Step S470 of FIG. 9 in the aforementioned embodiment of the present invention.

When the measurement results after the hematocrit correction of the whole blood thus obtained were compared with the measurement results of the blood plasmas, approximately the same measurement values were obtained. Therefore, it became clear that when the measurements are conducted by using the container (the general-purpose cartridge container) prepared by separately injecting commercially available reagents into an empty cartridge container for the present measuring equipment, the specimens of the whole blood can be measured by conducting corrections with the hematocrit values. The results are shown in Table 4.

TABLE 4

| specimen | blood plasma (IU/mL) | whole blood (IU/mL) | Ht value (%) | Ht correction value (IU/mL) | ratio to blood plasma (%) |
|---|---|---|---|---|---|
| No. 1 | 34 | 20 | 41.2 | 34 | 100.0 |
| No. 2 | 90 | 51 | 39.7 | 85 | 94.0 |

INDUSTRIAL APPLICABILITY

As described above, the present invention can provide highly versatile measuring equipment while maintaining the advantages of the special-purpose apparatus in that it is generally smaller than a general-purpose apparatus and capable of almost completely automating the operations by enabling the use of a general-purpose cartridge container prepared by separately injecting commercially available reagents into a cartridge container.

The invention claimed is:

1. A method for measuring items of a measurement object present in a specimen using a special-purpose cartridge container and a general-purpose cartridge container, each comprising a plurality of vessels, the method comprising:
   injecting separately into the plurality of vessels of the special-purpose cartridge container an amount of a predetermined reagent required for measurement of a specific item(s) of the measurement object in advance of the measurement and sealing the plurality of the vessels with a sealing material on which an information carrier is attached, where the information carrier includes information relevant to the specific item(s) of the measurement object; and
   injecting by an operator separately into at least one empty vessel of the general-purpose cartridge container an amount of a reagent required for measurement of an item(s) of the measurement object different from that of the item to be measured in the special-purpose cartridge container, wherein the plurality of vessels of the general-purpose cartridge container do not have attached an information carrier; reading out from a recording medium a control program for directing measuring equipment to decide from output from a carrier identification means whether the cartridge container is the special-purpose cartridge container or the general-purpose cartridge container; and
   conducting measurements in a manner such that when the cartridge container is the special-purpose cartridge container, the measurements are conducted by reading out measurement conditions from a measurement condition storage means based on the information relevant to the items of the measurement object included in the information carrier, whereas when the cartridge container is the general-purpose cartridge container, the measurements are conducted by outputting information relevant to selectable items of the measurement object so as to allow the operator to select the different items of the measurement object and reading out measurement conditions from the measurement condition storage means for the different items of the measurement object selected and input by the operator.

2. The method of claim 1, wherein a washing liquid is also injected separately into the plurality of vessels of the special-purpose cartridge container.

3. The method of claim 1, wherein the special-purpose cartridge container and the general-purpose cartridge container are each used for measuring only one specimen.

4. The method of claim 1, further comprising selecting an operation mode in a manner such that
   when an operation mode for an auxiliary operation is selected by the operator, a measurement operation procedure corresponding to an item of the measurement object is registered in the storage means, and
   when an operation mode for a start measurement is selected by the operator, the measurement is initiated based on the measurement operation procedure read out from the storage means.

5. The method of claim 1, wherein the specimen is blood or urine.

6. The method of claim 1, wherein the information carrier is an optically readable carrier.

7. The method of claim 6, wherein the optically readable carrier is a bar code.

8. The method of claim 1, wherein the recording medium is ROM, a flexible disc or a hard disc.

* * * * *